United States Patent [19]

Bjork et al.

[11] 4,024,264

[45] May 17, 1977

[54] DIPHENYLBUTYLPIPERIDINES

[75] Inventors: Anders Karl Konrad Bjork, Bjarred; Sven Erik Harry Hernestam, Malmo; Bengt Erik Sigvard Kjellberg, Staffanstorp, all of Sweden

[73] Assignee: AB Ferrosan, Malmo, Sweden

[22] Filed: Aug. 4, 1975

[21] Appl. No.: 601,412

[30] Foreign Application Priority Data

Aug. 15, 1974 United Kingdom ............ 35910/74
May 7, 1975 United Kingdom ............ 19222/75

[52] U.S. Cl. ............................. 424/267; 260/293.8
[51] Int. Cl.² ............ C07D 211/30; C07D 211/50
[58] Field of Search ................ 260/293.8; 424/267

[56] References Cited

UNITED STATES PATENTS

| | | | |
|---|---|---|---|
| 3,029,244 | 4/1962 | Lyle et al. | 260/293.8 |
| 3,632,767 | 1/1972 | Gray et al. | 260/293.79 |
| 3,793,334 | 2/1974 | Ebnoether et al. | 260/293.8 |
| 3,795,677 | 3/1974 | Carr et al. | 260/293.8 |

*Primary Examiner*—Norma S. Milestone
*Attorney, Agent, or Firm*—Gordon W. Hueschen

[57] ABSTRACT

Novel 4,4-diphenylbutyl-1-(4-benzoyl-4-hydroxy or acyloxy)-piperidines and acid addition salts thereof, useful as central depressants, e.g., neuroleptics (antipsychotics), are disclosed. Methods of making same, pharmaceutical compositions thereof, a method of treating therewith, and important and novel intermediates for the production thereof, namely, 4-benzoyl-4-hydroxypiperidines, are also disclosed, as well as 4-benzoyl-1-(4,4-diphenylbutyl)-piperidines, which are also useful intermediates.

54 Claims, No Drawings

DIPHENYLBUTYLPIPERIDINES

BACKGROUND OF INVENTION

1. Field of the Invention 4,4-diphenylbutyl-1-(4-benzoyl-4-hydroxy or acyloxy) piperidines and acid addition salts thereof; central depressant, neuroleptic compounds; 4-benzoyl-4-hydroxypiperidine and other intermediates therefor.

2. Prior Art

A number of ketones of the general formula

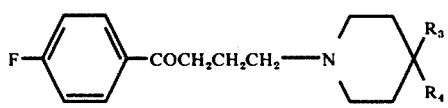

wherein $R_3$ and $R_4$ are widely different groups, have been made and tested. As to these type compounds, Janssen (Cavallito; "Structure-Activity Relationships I", page 37) has stated that one of the groups $R_3$ and $R_4$ must be aromatic and that only one may be hydrogen if the ketone is to be an anti-psychotic.

For comparison with the compounds of the present invention, we have used three clinically-established compounds, namely:

Haloperidol, of the foregoing formula, wherein $R_3 =$ OH and $R_4 =$

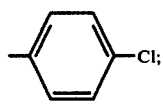

Chloropromazine, having the formula

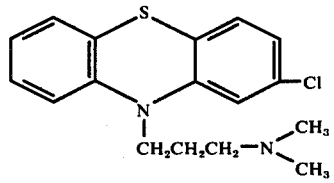

and Pimozide, having the formula

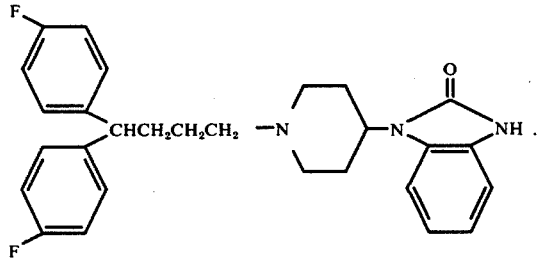

These established clinically-useful compounds of the prior art have, however, been found to be characterized by pronounced shortcomings and side-effects, and there is a clear demand for more specific and advantageous compounds in this activity and utility area, especially as neuroleptics (anti-psychotics). The fulfillment of this demand is one of the objects of the present invention, as will become more fully apparent hereinafter.

SUMMARY OF THE INVENTION

This invention relates to novel 4,4-diphenylbutyl-1-(4-benzoyl-4-hydroxy or acyloxy)-piperidines, acid addition salts thereof, pharmaceutical compositions containing the same, a method of using the same as neuroleptics, and a process for the manufacture thereof, as well as novel intermediates, e.g., 4-benzoyl-4-hydroxypiperidines. The novel compounds provided by the present invention are selected from the group consisting of (a) 4,4-diphenylbutyl-1-(4-benzoyl-4-hydroxy or acyloxy)-piperidines, having the general formula

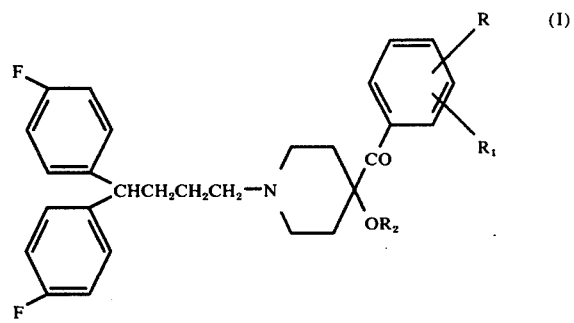

wherein R and $R_1$ independently represent hydrogen or a loweralkyl group with 1 to 5 carbon atoms, inclusive, halogen including F, Cl, and Br, lower-alkoxy having 1–5 carbon atoms, inclusive, or —$CF_3$, and $R_2$ represents hydrogen or an acyl (Ac) group having 1 to 19 carbon atoms, inclusive, and b. acid addition salts thereof.

These novel compounds of Formula I have valuable pharmacological properties, especially central depressant effects as further elucidated hereinafter, which makes them useful as neuroleptics (i.e., anti-psychotically-active substances).

OBJECTS

It is an object of the present invention to provide novel 4,4-diphenylbutyl-1-(4-benzoyl-4-hydroxy or acyloxy)-piperidines and acid addition salts thereof, which are useful as central depressants, e.g., neuroleptics (anti-psychotics), a process for producing the same, pharmaceutical compositions thereof, intermediates therefor, and a method of treating psychotic states therewith. Additional objects will become apparent hereinafter, and still others will be obvious to one skilled in the art.

PREPARATION

According to the present invention, the novel compounds of General Formula I are prepared:

ROUTE 1 a. by reaction of a 4-benzoylpiperidine II

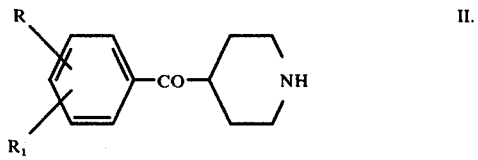

with the compound

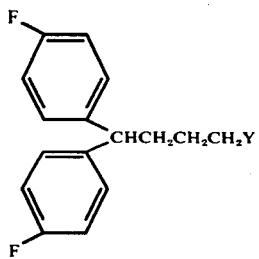
III.

wherein Y is halogen, e.g., Cl or Br, preferably Br, or another reactive group, e.g.,

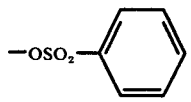

or tosyl, to produce the compound

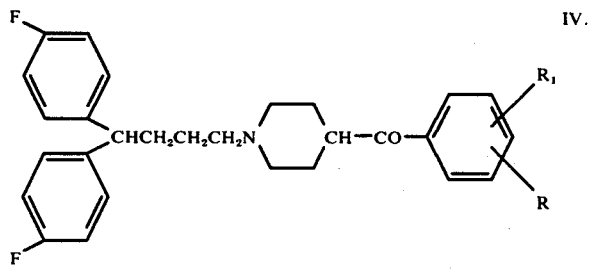
IV.

and then introducing the OR$_2$ group, i.e., the hydroxy or acyloxy group, into the 4-position of the piperidino radical, preferably by first brominating to produce the compound

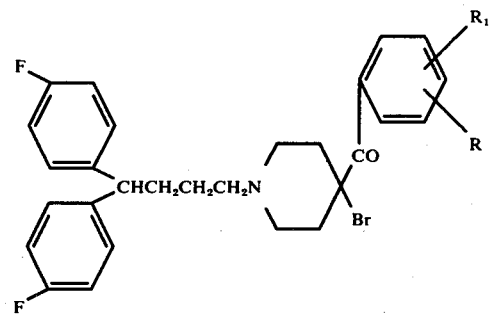
V.

followed by debromination with e.g., sodium methoxide in methanol, to produce the compound

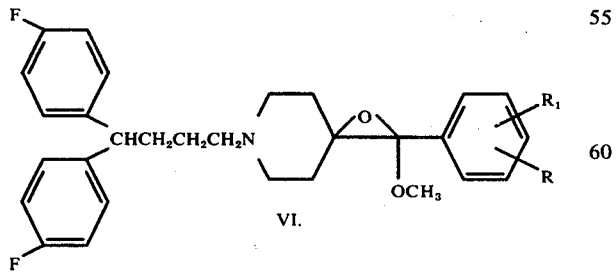
VI.

and then hydrolyzing to the hydroxy compound I, wherein R$_2$=H, after which the hydroxy compound may be acylated, if desired, in conventional manner, to produce the corresponding acyloxy compound I wherein R$_2$ is acyl; or

ROUTE 2 b 1. by reacting the 4-benzoylpiperidine VII

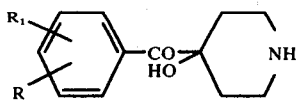
VII.

with the compound III to produce the corresponding compound I, or

ROUTE 3 b 2. by reacting the 4-benzoylipiperidine VII with the compound VIII

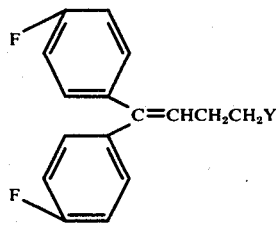
VIII.

wherein Y has the meaning previously assigned, to produce the compound

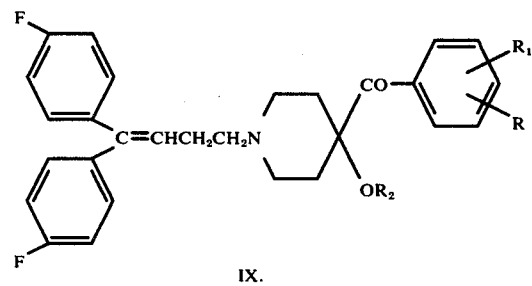
IX.

and selective reduction to produce compound I; or

ROUTE 4 c 1. By reacting compound III with

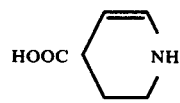

or an ester thereof to produce the compound

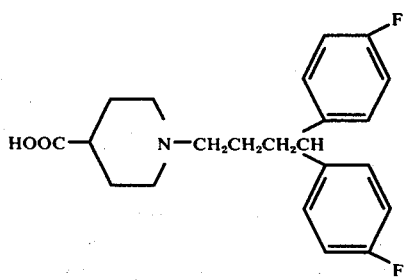
X.

converting the carboxy group or an ester thereof to the acid chloride and performing a Friedel-Crafts reaction thereon with AlCl₃ and a substituted benzene of the formula RR₁-benzene to produce the compound of formula IV, or

ROUTE 5 c 2. by reacting compound VIII in the same manner as given in (c 1) and then selectively reducing to produce compound X.

Of the described methods, a) and b 1) are preferred, and the synthesis can always be carried out with one of these methods.

The starting compounds

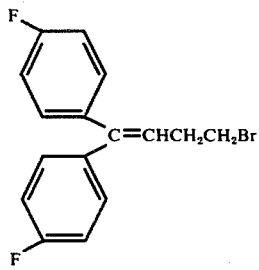

VIII and

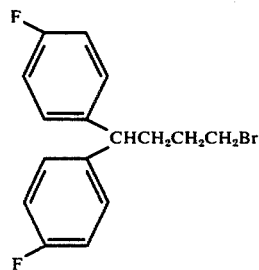

III are synthesized according to French Patent M 3695 (CA 66, 115 709).

The benzoylpiperidine II and the novel 4-benzoyl-4hydroxypiperidine VII, both of which are intermediates in the process of the invention, can be prepared by a sequence of reactions starting with isonipecotic acid and proceeding via the 1-acetylisonipecotic acid or 1-methylisonipecotic acid and its acid chloride. This latter compound is then reacted with a suitable known RR₁-substituted benzene compound as follows: IA) a Friedel-Crafts reaction of

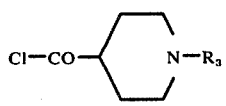

wherein R₃ is acetyl and an RR₁-substituted benzene in a suitable reaction solvent, e.g., nitrobenzene or an excess of the reacting compound RR₁-benzene, to produce a compound

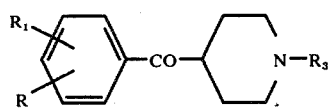

XI whereupon the acetyl group (XI, R₃ = CH₃CO) is removed with 5-N HCl to produce the compound II, or I B) a Grignard reaction of 4-cyanopyridine and a suitable known phenyl magnesium bromide or other halide of the formula RR₁-phenyl-Mg X to produce the compound

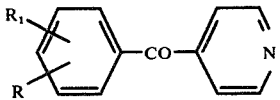

XII the 4-benzoylpyridine XII is then either (a) hydrogenated over platinum catalyst to give the 4-piperidylarylcarbinol

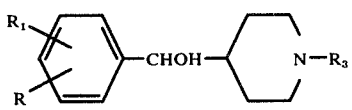

XIII wherein R₃ represents hydrogen, or (b) first benzylated or methylated to the corresponding 1-benzyl- (or methyl) 4-aroylpyridinium halide and then reduced to compound XIII (R₃=benzyl or CH₃).

Compound XIII is then oxidized by chromic oxide or another oxidizing acid in acetic acid to the compound II (R₃ = H) or compound XI (R₃ = CH₃ or benzyl).

The crude 4-aroylpiperidines XI (R₃ =CH₃ or benzyl) are converted to the hydrobromides. Compound XI (R₃ =H) is acetylated.

Compound XI (R₃ =CH₃, benzyl, or CH₃CO) is dissolved in a suitable solvent, e.g., CHCl₃ or CCl₄, and is brominated with Br₂ to produce the compound

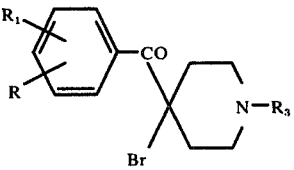

XIV which, after recrystallization, is treated wtih NaOMe in MeOH. After addition of water and evaporation of MeOH, the compound

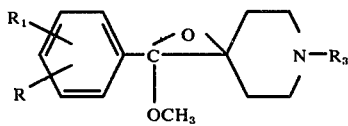

XV may be extracted with ether. The crude compound XV is hydrolized in ethanol with concentrated hydrochloric acid to produce the compound

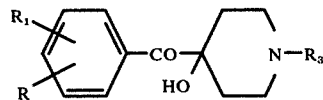

XVI

Compound XVI (R₃ =CH₃CO) is precipitated with water. After alkalization, extraction with CHCl₃ or benzene, and drying of the solution with Na₂SO₄, compound XVI (R₃ =CH₃ or benzyl) can be precipitated with an acid addition salt.

The novel intermediate VII is then prepared from XVI by:

II A. removal of the acetyl group (XVI, $R_3$=$CH_3CO$) using 5-N HCl. Other strong mineral acids may also be used.

II B. selective hydrogenolysis over palladium catalyst of the benzyl group (XVI, $R_3$ = benzyl)

II C. demethylation (XVI, $R_3$ = $CH_3$) with ethyl chloroformate, followed by acid hydrolysis.

In more detail, the starting benzoylpiperidine II is synthesized according to Duncan et al., Med. Chemistry 13, (1), 1 (1970), e.g., by a Friedel-Crafts reaction of

and a suitable known $RR_1$-substituted benzene in a suitable solvent, e.g., nitrobenzene or an excess of the reacting compound $RR_1$-benzene itself, to produce a compound of the formula XI, whereupon the Ac-group is removed with 5-N HCl. In reaction a), the benzoylpiperidine II is reacted with compound III in a suitable solvent, which may be a non-polar solvent, such as benzene or xylene, or a polar solvent, e.g, dimethylformamide or butylacetate.

The reaction a) is preferably performed in the presence of an acid-binding agent such as triethylamine, $K_2CO_3$, and advantageously but not necessarily in an autoclave at 75°–150° C.

After the coupling reaction, the products are generally treated with water or 1-N NaOH and extracted with ether, methyl-butyl ketone, or the like. From the dried solution, the hydrobromides or hydrochlorides may be precipitated and recrystallized. Even the crude product may be used for further reaction, if desired.

The acid salt, e.g., hydrobromide, is dissolved in a suitable solvent, e.g., carbon tetrachloride or chloroform, and brominated with $Br_2$ to produce compound V, which without further purification can be heated with sodium methoxide in methanol. After addition of water and evaporation of the solvent, compound V may be extracted with ether. The crude compound is hydrolized in ethanol with concentrated hydrochloride acid and, after alkalization, extraction with ether and drying of the solution with sodium sulfate, the compound I can be precipitated as a salt, preferably with a pharmaceutically acceptable acid, e.g., hydrochloric or hydrobromic acid, oxalic acid, maleic acid, citric acid, tartaric acid, or the like. One acid salt, even if not pharmaceutically acceptable, can be readily converted to another salt which is pharmaceutically acceptable in known manner, if desired.

DETAILED DESCRIPTION OF THE INVENTION

The following Preparations and Examples are given by way of illustration only.

PREPARATION 1: 1-ACETYLISONIPECOTIC ACID AND ITS ACID CHLORIDE

A solution of 64.6 g (0.5 mole) of isonipecotic acid in 200 ml of acetic anhydride was refluxed for two hours and allowed to stir at room temperature overnight. The solution was concentrated and the residue which remained was triturated in ether. The solid was collected by filtration and recrystallized from isopropyl alcohol – isopropyl ether. Yield 58.2 g., melting point 178°–182° C. (Reference: Duncan, R.L. et al., J. Med. Chem., 13, (1), 1 (1970). This compound is converted to its acid chloride by the following detailed procedure:

To 400 ml of $SOCl_2$ was added 68.9 g (0.4 mole) of 1-acetylisonipecotic acid, which dissolved. The acid chloride precipitated from solution and 1 liter of pentane was added. The mixture was filtered and the solid residue was washed several times with pentane. The solid was dried. Yield 72 g.

PREPARATION 2: 1-ACETYL-4-(p-FLUOROBENZOYL)PIPERIDINE

To a stirring mixture of 55.0 grams (0.41 mole) of aluminum chloride in 100 ml. fluorobenzene was slowly added forty grams (0.21 mole) of 1-acetyl-isonipecotyl chloride. After the addition was complete, the mixture was refluxed for 1 hour. The mixture was poured onto ice and the two resulting layers were separated. The aqueous layer was extracted with chloroform and the extracts were added to the fluorobenzene. The organic solution was dried over sodium sulfate and filtered. The filtrate was concentrated under reduced pressure and the residue was a crystalline solid. The reaction product was purified by recrystallization in ligroin-isopropylether. Yield: 38.2 grams; melting point: 76°–80° C. (Reference: Duncan, R. L., et al., J. Med.Chem. 13 (1) 1 (1970).

In exactly the same manner, the following additional compounds are prepared, starting only from the appropriate benzene:

1-acetyl-4-benzoylpiperidine from benzene itself;
1-acetyl-4-(p-methoxybenzoyl)piperidine from methoxybenzene;
1-acetyl-4-(p-bromobenzoyl)piperidine from bromobenzene;
1-acetyl-4-(p-chlorobenzoyl)piperidine from chlorobenzene; and
1-acetyl-4-(p-methylbenzoyl)piperidine from methylbenzene.

PREPARATION 3: 4-(p-FLUOROBENZOYL)PIPERIDINE HYDROCHLORIDE (Compound II)

A solution of fifty g. (0.2 mole) of 1-acetyl-4-(p-fluorobenzoyl)piperidine in 200 ml of 6 N HCl was refluxed for twelve hours. The cooled solution was extracted twice with ether. The aqueous solution was made basic (NaOH) and then extracted with benzene. The benzene extracts were dried ($Na_2SO_4$) and filtered. The filtrate was concentrated under reduced pressure, and the residual oil was converted to the hydrochloride salt. The crude product was recrystallized from isopropyl alcohol. Yield 42 g., melting point 223°–25° C. (Reference: Duncan, R. L., et al., J.Med.Chem., 13 (1) 1 (1970).

In exactly the same manner, the following additional compounds are prepared by substituting the appropriate starting 1-acetyl-4-benzoylpiperidine from Preparation 2 in the procedure of Preparation 3:

|  | m.p. |
| --- | --- |
| 4-benzoylpiperidine hydrochloride | 222–224° C |
| 4-(p-methoxybenzoyl)piperidine hydrochloride | 255–258° C |
| 4-(p-bromobenzoyl)piperidine hydrochloride | 228–230° C |
| 4-(m-trifluoromethylbenzoyl)piperidine hydrochloride | |
| 4-(3-trifluoromethyl-4-chlorobenzoyl)piperidine hydrochloride | 238–240° C |
| 4-(p-methylbenzoyl)piperidine hydrochloride | 260–263° C | and so on.

PREPARATION 4:
4-(p-FLUOROBENZOYL)-1-[4,4-(DI-p-FLUOROPHENYL)-BUTYL]PIPERIDINE HYDROBROMIDE (Compound IV)

A stirred mixture of 6.2 g (0.03 mole) of 4-(p-fluorobenzoyl)-piperidine (Compound II), 9.8 g (0.035 mole) of 4-chloro-1,1-(di-p-fluorophenyl)butane, 10 grams of anhydrous sodium carbonate, 0.15 g. of potassium iodide, and 250 ml. of isobutyl acetate was heated at reflux for 85 hours. The mixture was filtered and the filtrate was concentrated under vacuum. The residual oil was dissolved in ether and the hydrobromide was precipitated with ethanolic HBr. The reaction product was purified by recrystallization from ethanolether. Yield: 12.8 g, melting point 147° C.

Additional intermediates of this type IV, which can be produced in the same manner from the respective suitable starting materials, are set forth in Table II.

PREPARATION 5:
4-BROMO-4-(p-FLUOROBENZOYL)-1-[4,4-(DI-p-FLUOROPHENYL)BUTYL]-PIPERIDINE HYDROBROMIDE

A solution of 10.6 g (0.02 mole) of 4-(p-fluorobenzoyl)-1-[4,4-(di-p-fluorophenyl)butyl]piperidine hydrobromide in fifty ml. of chloroform was treated with 3.4 ml. of bromine. The reaction mixture was allowed to stand for 17 hours at room temperature. The solvent and excess bromine were removed under reduced pressure. The residue was dissolved in a solution containing 6.5 g. phenol in 100 ml. of methanol, and the solution was diluted with anhydrous ether precipitating the 4-bromo-4-(p-fluorobenzoyl)-1-[4,4-(di-p-fluorophenyl)butyl]piperidine hydrobromide. The reaction product was purified by recrystallization from methanol-ether. Yield: 10 g.; melting point 160° C.

Additional intermediates of this same type are produced in the same manner from the appropriate starting materials.

PREPARATION 6:
2-(p-FLUOROPHENYL)-6-[4,4-(DI-p-FLUOROPHENYL)BUTYL]-2-METHOXY-1-OX-6-AZASPIRO[2.5]OCTANE

A solution of ten grams (0.019 mole) of 4-bromo-4-(p-fluorobenzoyl)-1-[4,4-(di-p-fluorophenyl)butyl]-piperidine hydrobromide in 35 ml. of methanol was added to a solution of sodium methoxide prepared from the three grams of sodium in 35 ml. of methanol. The mixture was heated under reflux for 4 hours, and most of the methanol was removed under reduced pressure. Water was added, and the remaining methanol was removed under reduced pressure. The aqueous layer was extracted with ether, and the extracts were dried over sodium carbonate. Removal of the ether gave crude 2-(p-fluorophenyl)-6-[4,4-(di-p-fluorophenyl)butyl]-2-methoxy-1-oxo-6-azaspiro [2.5] octane. Yield: 6.7 g.

Additional intermediates of this same type are produced in the same manner from the appropriate starting materials.

EXAMPLE 1:
4-(p-FLUOROBENZOYL)-4-HYDROXY-1-[4,4-(DI-p-FLUOROPHENYL)-BUTYL]PIPERIDINE OXALATE (Compound I)

A mixture of 4.8 g. (0.01 mole) of 2-(p-fluorophenyl) -6-[4,4-(di-p-fluorophenyl)butyl]-2-methoxy-1-oxo-6-azaspiro [2.5] octane, five ml. of concentrated hydrochloric acid and thirty ml of ethanol was stirred for ten minutes. Water was added, and most of the ethanol was removed under reduced pressure. Neutralization with sodium carbonate and extraction with chloroform gave crude 4-(p-fluorobenzoyl)-4-hydroxy-1-[4,4-(di-p-fluorophenyl)butyl]piperidine. The obtained base was dissolved in ethanol and the oxalate was precipitated by addition of oxalic acid dissolved in ethanol. The reaction product was purified by recrystallization from ethanol. Yield: 4.4g; melting point 214° C.

Additional end products of this type I, which can be produced in the same manner from the respective suitable starting materials, are set forth in Table III.

EXAMPLE 2:
4-(p-FLUOROBENZOYL)-4-PROPIONYLOXY-1-[4,4-(DI-p-FLUOROPHENYL)-BUTYL]PIPERIDINE HYDROCHLORIDE

Two grams of the crude base from EXAMPLE 1 is dissolved in twenty ml. of propionic anhydride and a catalytic amount of 4-dimethylaminopyridine is added. After 10 hours at 20° C., the solvent is evaporated. The remainder is dissolved in ethylacetate-ether and treated with ethanolic HCl. The obtained hydrochloride is recrystallized from ethanol. The melting point is 246-248° C.

EXAMPLE 3:
4-(p-METHYLBENZOYL)-4-HYDROXY-1-[4,4-(DI-p-FLUOROPHENYL)BUTYL]PIPERIDINE HYDROCHLORIDE

This compound is synthesized in the same manner as given in EXAMPLE 1 starting from 4-(p-methylbenzoyl)piperidine instead of 4-(p-fluorobenzoyl)piperidine. The hydrochloride has the melting point 120°-122° C.

EXAMPLES 4 -11

In the same manner, as shown in the following Table III, the following end products are produced, starting only with the suitable selected starting benzoylpiperidine II or, as shown in the following EXAMPLE 12, starting from the suitable selected 4-benzoyl-4-hydroxypiperidine VII of PREPARATION 10:

4. 4-(p-Methoxybenzoyl)-4-hydroxy-1-[4,4-(di-p-fluorophenyl)-butyl]piperidine oxalate.
5. 4-(p-Bromobenzoyl)-4-hydroxy-1-[4,4-(di-p-fluorophenyl)-butyl]piperidine hydrochloride.
6. 4-(m-Trifluoromethylbenzoyl)-4-hydroxy-1-[4,4-(di-p-fluorophenyl)butyl]piperidine oxalate.
7. 4-(3-Trifluoromethyl-4-chlorobenzoyl)-4-hydroxy-1-[4,4-(di-p-fluorophenyl)butyl]piperidine hydrochloride.
8. 4-Benzoyl-4-hydroxy-1-[4,4-(di-p-fluorophenyl butyl]-piperidine hydrochloride.
9. 4-(p-Chlorobenzoyl)-4-hydroxy-1-[4,4-(di-p-fluorophenyl)-butyl]piperidine hydrochloride.
10. 4-(p-Fluorobenzoyl)-4-decanoyloxy-1-[4,4-(di-p-fluorophenyl)-butyl]piperidine hydrochloride.

This compound is obtained following the procedure of EXAMPLE 2 by substituting decanoic acid anhydride or chloride for propionic anhydride.

11. 4-(p-Fluorobenzoyl)-4-nonadecanoyloxy-1-[4,4-(di-p-fluorphenyl)-butyl]piperidine hydrochloride.

This compound is obtained following the procedure of EXAMPLE 2 by substituting nonadecanoic acid anhydride or chloride for propionic anhydride.

PREPARATION 7:
1-ACETYL-4-BROMO-4-(p-FLUOROBENZOYL)-PIPERIDINE

A solution of 36 g. (0.145 mole) of 1-acetyl-4-(p-fluorobenzoyl)piperidine in 175 ml of chloroform was treated with fifteen ml. of bromine. The mixture was heated at reflux for one hour and was then allowed to stand overnight at room temperature 1-Acetyl-4-bromo-4-(p-fluorobenzoyl)piperidine hydrobromide precipitated and was collected by filtration and recrystallized from ethanol. Yield: 40.6 g., melting point 156°–159° C. In exactly the same manner, additional intermediates of this type are produced by substituting the selected starting materials from PREPARATION 2 in the procedure of PREPARATION 7.

PREPARATION 8:
6-ACETYL-2-(p-FLUOROPHENYL)-2-METHOXY-1-OX-6-AZASPIRO [2.5] OCTANE 32.8 g (0.1 mole) of 1-acetyl-4-bromo-4-(p-fluorobenzoyl)piperidine was added to a solution of sodium methoxide prepared from 12.8 g. of sodium in 400 ml. of methanol. The mixture was heated at reflux for 2 hours. Water was added and the methanol was removed under reduced pressure. The aqueous layer was extracted with ether and the extracts were dried over sodium carbonate. Removal of the ether gave crude 6-acetyl-2-(p-fluorophenyl)-2-methoxy-1-ox-6-azaspiro [2.5] octane. Yield: 24.2 grams. In exactly the same manner, additional intermediates of this type are produced by substituting the selected starting materials from PREPARATION 7 in the procedure of PREPARATION 8.

PREPARATION 9:
1-ACETYL-4-(p-FLUOROBENZOYL)-4-HYDROXYPIPERIDINE

A mixture of 21.3 g. (0.076 mole) of 6-acetyl-2-(p-fluorophenyl)-2-methoxy-1-ox-6-azaspiro [2.5] octane, 140 ml. of ethanol and 27 ml. of concentrated hydrochloric acid was stirred for fifteen minutes. Water was added. The solid which precipitated was collected by filtration and recrystallized from ethanol-ether giving nineteen grams of 1-acetyl-4-(p-fluorobenzoyl)-4-hydroxy-piperidine. Melting point: 146°–149° C. In exactly the same manner, additional intermediates of this type are produced by substituting the selected starting materials from PREPARATION 8 in the procedure of PREPARATION 9.

PREPARATION 10:
4-(p-FLUOROBENZOYL)-4-HYDROXY-PIPERIDINE HYDROCHLORIDE (Compound VII)

A solution of 18.6 grams (0.07 mole) of 1-acetyl-4-(p-fluorobenzoyl)-4-hydroxy-piperidine in sixty ml. of 5-N HCl was refluxed for 15 hours. Nost of the water was removed under reduced pressure. Ethanol was added and the solution was cooled. The solid which precipitated was collected by filtration and recrystallized from ethanol giving 16.5 grams of 4-(p-fluorobenzoyl)-4-hydroxy-piperidine hydrochloride. Melting point: 241°–243° C.

In exactly same manner, the following additional compounds are prepared by substituting the appropriate starting 1-acetyl-4-benzoyl-4-hydroxypiperidine from PREPARATION 9 in the procedure of PREPARATION 10:

4-benzoyl-4-hydroxypiperidine hydrochloride
4-(p-methoxybenzoyl)-4-hydroxupiperidine hydrochloride
4-(p-bromobenzoyl)-4-hydroxypiperidine hydrochloride
4-(m-trifluoromethylbenzoyl)-4-hydroxypiperidine hydrochloride
4-(3-trifluoromethyl-4-chlorobenzoyl)-4-hydroxypiperidine
4-(p-chlorobenzoyl)-4-hydroxypiperidine hydrochloride
4-(p-methylbenzoyl)-4-hydroxypiperidine hydrochloride, and so on.

EXAMPLE 12:
4-(p-FLUOROBENZOYL)-4-HYDROXY-1-[4,4-(DI-p-FLUOROPHENYL)BUTYL]PIPERIDINE OXALATE AND HYDROCHLORIDE (Compound I)

A stirred mixture of eleven grams (0.05 mole) of 4-(p-fluorobenzoyl)-4-hydroxypiperidine, 16.9 grams (0.06 mole) of 4-chloro-1,1-(di-p-fluorphenyl)butane, twenty grams of anhydrous potassium carbonate, and 300 ml. of isobutylacetate was heated at reflux for 60 hours. The mixture was filtered and the filtrate was concentrated under vacuum. The residual oil as dissolved in ethanol and the oxalate was precipitated with oxalic acid dissolved in ethanol. The crude product was purified by recrystallization in ethanol. Yield: fifteen grams; melting point 214° C. The compound is converted to its hydrochloride salt in conventional manner by neutralization and acidification with HCl according to the general procedure given in EXAMPLE 2.

In the same manner, the following additional compounds of Type I and their acid addition salts, e.g., their hydrochlorides, oxalates, hydrobromides, citrates, or tartrates, are prepared by employing the selected starting 4-benzoyl-4-hydroxypiperidine from PREPARATION 10 in the procedure of EXAMPLE 12:

4-(p-Methylbenzoyl)-4-hydroxy-1-[4,4-(di-p-fluorophenyl)butyl]piperidine
4-(p-Methoxybenzoyl)-4hydroxy-1-[4,4-(di-p-fluorophenyl)-butyl]piperidine
4-(p-Bromobenzoyl)-4-hydroxy-1-[4,4-(di-p-fluorophenyl)butyl]piperidine
4-(m-Trifluoromethylbenzoyl)-4-hydroxy-1-[4,4-(di-p-fluorophenyl)butyl]piperidine.
4'-(3-Trifluoromethyl-4-chlorobenzoyl)-4-hydroxy-1-(4,4(di-p-fluorophenyl)butyl]piperidine.
4-Benzoyl-4-hydroxy-1-[4,4-(di-p-fluorophenyl)-butyl]-piperidine.
4-(p-Chlorobenzoyl)-4-hydroxy-1-[4,4-(di-p-fluorophenyl)-butyl]piperidine.

EXAMPLE 13:
4-(p-METHYLBENZOYL)-4-DIMETHYLACETOXY-1-[4,4-(DI-p-FLUOROPHENYL)-BUTYL]PIPERIDINE HYDROCHLORIDE

In the same manner as given in EXAMPLE 2, this product is produced from the product of EXAMPLE 3 and dimethylacetylchloride or anhydride.

In the same manner as given in EXAMPLES 2, 10, 11, and 13, additional 4-acyloxy compounds of any Type I compounds, as set forth in Table III, are produced from the appropriate 4-hydroxy compound and the selected acyl halide or anhydride, including the acetates, propionates, butyrates, caproates, valerates, octanoates, decanoates, dodecanoates, hexadecanoates, octodecanoates, nonadecanoates, and the like.

Moreover, in addition to the substituent $R_1$ shown in Table III, the same and/or additional R substituents may be present in different and varying ring positions, e.g., in a different position or as the second substituent in the benzene ring in addition to the $R_1$ substituent already present therein, such as fluoro, bromo, methyl. methoxy. trifluoromethyl, ethyl, chloro, amyl, ethoxy, amyloxy, or the like, depending only upon a judicious selection of the ring positions and substituents present in a starting disubstituted benzene compound to be employed in PREPARATION 2, as will be apparent and within the ability of anyone skilled in the art, including the acid addition salts, e.g., the hydrochlorides, hydrobromides, oxalates, citrates, or tartrates of such compounds.

PHARMACOLOGY

Representative compounds of the present invention have been subjected to a series of pharmacological tests, in which the new compounds were compared with Haloperidol, Chlorpromazine, and Pimozide, havin the formulas previously given. The pharmacological tests used are suitable for measuring:

1. Inhibition of aggressive behaviour-in-male mice
2. Inhibition of climbing-in-mice (inhibition of exploratory behaviour)
3. Amphetamine antagonism-in-rats (antipsychotic effect)
4. Cataleptogenic effect-in-rats (measure of extrapyramidal side effects)
5. Inhibition of conditioned behaviour-in-rats These tests 1-5 have been described, and the importance of coordinating the compounds with these tests and the activities shown thereby is described in detail in the following literature:

1. Inhibition of Aggression
   Valzelli, L. in Aggressive Behaviour, Eds. Garattini and Sigg, p. 70 (1969), Valzelli, L. in Neuro-Psycho-Pharmacology, Ed. Brill, p. 781 (1967).

2. Inhibition of Exploratory Behaviour (Climbing)
   van Rossum, J. M. et al. in The Neuroleptics, Modern Problems of Psyco-Psychiatri, Vol. 5, p.26 (1970), Kneip, P. in Arch. Int. Pharmacodyn, 126, 238 (1960), Sandberg, S. in Arzneimittelforschung, 9, 203 (1958).

3. Amphetamine Antagonism
   Randrup, A. et al. in Acta Pharmacol. (Kph), 20, 145 (1963), Randrup, A. in The Neuroleptics, Modern Problems of Psycho-Psychiatri, Vol. 5, p. 60 (1970).

4. The Cataleptogenic Effect
   Rossum, J.M. et al. in The Neuroleptics, Modern Problems of Psycho-Psychiatry, Vol. 5, p. 26 (1970), Stille, C. in Schweiz. Med. Wochenschrift 99,1645 (1969), 5. Inhibition of Conditioned Avoidance Response
   "Neuroleptics characteristically interrupt the response to the warning stimulus (avoidance) without at the same time interrupting the response to the noxious stimulus (escape) which follows it" An Introduction to Psycho-Pharmacology, Eds. Rech and Moore, New York, p. 264 (1971), Courvoisier, S. et al. in Arch. Int. Pharmacodyn., 92, 305 (1953) Jacobsen, E. in Psychotrophic Drugs, Eds. Garattini, Ghetti, Amsterdam, p. 119 (1957) Jacobsen and Sonne in Acta Pharmacol. & Toxicol. 11, pp. 135–147 (1955).

The results are tabulated in Table I.

TABLE I

| $R_1$ | $R_2$ | R | 1<br>Inhib. of aggression<br>4 hours | 2<br>Inhib. of expl. activity<br>4 hours | 3<br>Amphetamine Antagonism<br>4 hours | 4<br>Catalepsy<br>4 hours | 5 x)<br>Inhib. of conditioned avoidance<br>4 hours |
|---|---|---|---|---|---|---|---|
| Haloperidol | | | 0.8 | 0.7 | 0.06 | 0.11 | 0.2 |
| Chlorpromazine | | | 0.5 | 0.9 | 1.6 | 3.6 | 5.2 |
| Pimozide | | | 0.3 | 6.8 | 0.13 | 2.0 | 0.6 |
| F | H | H | 1.5 | 10 | 0.2 | >20 | 2.2 |
| $CH_3$ | H | H | 2.3 | 20 | 2.0 | >20 | 20 |
| F | —$COC_2H_5$ | H | 1.7 | 20 | 2.0 | >50 | 20 | x) The figures refer to the numbers given to these pharmacological tests in the text.

In special experiments on monkeys, the new compounds produce very few or no extrapyramidal side effects at all in contrast to, e.g., haloperidol and chlorpromazine, which induce such side effects readily and at low doses.

Furthermore, the duration of activity of the new compounds is around 24 hours, a figure which is comparable to that for pimozide, whereas the duration of action of haloperidol and chlorpromazine is around 6-8 hours.

The actue toxicity of the new compounds according to the invention determined orally in conventional manner, is rather low, ranging from 350 mg/kg to more than 800 mg/kg. For comparison it may be mentioned that the acute toxicity for haloperidol is 70 mg/kg and for chlorpromazine 280 mg/kg.

The antipsychotic effect as shown in Test No. 3 is further confirmed by the blocking of apomorphineinduced emesis in dogs.

On account of these favorable properties, the new compounds are indicated for the treatment of certain mental disturbances in humans, for instance schizophrenia, mania, anxiety, agony, and aggression. Their general tranquilizing properties also make the new compounds suitable for veterinary applications.

The high order of activity of the active agents of the present invention has been evidenced by tests in lower animals and representative of these are reported herein.

The novel compounds are preferably used in the form of their pharmaceutically-acceptable acid addition salts, e.g., their hydrochlorides, hydrobromides, or the like. The salt form is als the best form for pharmaceutical formulations. Innumerable other pharmaceutically-acceptable acid addition salts can be prepared from the hydrochlorides via the free bases in conventional manner. For oral use, the compounds are usually administered as tablets in which they are present together with usual pharamceutical carriers, excipients, binders, and the like. For example, tablets may be prepared conventionally by compounding one of the new compounds, preferably in the form of an acid addition salt thereof, with customary carriers and adjuvants, e.g., talc, magnesium stearate, starch, lactose, gelatin, gums, and the like.

In their most advantageous form, then, the compositions of the present invention will contain a non-toxic pharmaceutical carrier in addition to the active ingredient of Formula I. Exemplary carriers are: solids-lactose, magnesium stearate, calcium stearate, starch, terra alba, dicalcium phosphate, sucrose, talc, stearic acid, gelatin, agar, pectin, acacia, or the like; liquids - peanut oil, sesame oil, olive oil, water, or the like. The active agents of the invention can be most conveniently administered in such compositions containing about 0.01 to 67 percent, preferably 0.04 to 12.15 percent, by weight of the active ingredient. Such formulations are representatively illustrated in U.S. Pat. No. 3,402,244.

A wide variety of pharmaceutical forms suitable for many modes of administration and dosages may be employed. For oral administration the active ingredient and pharmaceutical carrier may, for example, take the form of a granule, pill tablet, lozenge, elixir, syrup, or other liquid suspension or emulsion; for parenteral administration, the composition may be a sterile solution; and for rectal administration, a suppository.

The method of using the compounds of the present invention comprises internally administering a compound of Formula I, usually in the form of a non-toxic, pharmacologically acceptable acid-addition salt, and preferably admixed with a pharmaceutical carrier, for example, in the form of any of the above-mentioned compositions, or filled into a capsule, to alleviate psychotic conditions and symptoms thereof in a living animal body, for example, the aforementioned schizophrenic, manic, anxiety, agony, and aggressive states. The compounds and their non-toxic salts, especially the hydrochlorides, may be advantageously employed in amounts approximating those employed for any of the three clinically-useful compounds used for comparative testing as reported herein. Illustratively, they may be used in an amount of from about 0.1 to 200 milligrams per unit dose, preferably from about 2.5 to 50 milligrams for an oral dose, while parenteral dosages are usually less and ordinarily about one-half the oral dose so that the preferred parenteral unit dosage will be about one to 25 milligrams. The unit dose is preferably given a suitable number of times daily so that the daily dose may vary from 0.3 to 600 milligrams. Preferred daily dosages will vary from about 7.5 to 150 milligrams (oral) to about three to 75 milligrams (parenteral). However, these compounds are subject to wide variations in optimum daily and unit dosages, due to patient body weight, condition, and ancillary factors and the invention should therefore not be limited by the exact ranges stated. The exact dosage, both unit and daily, will of course have to be determined according to established medical principles. In addition, the active ingredients of the present invention or compositions containing the same may either be administered together with or include other physiologically active materials and/or medicaments, e.g., buffering agents, antacids, sedatives, stimulants, anticholinergics, analgesics, or the like.

The following formulations are representative for all of the pharmacologically active compounds of the invention, but have been particularly designed to embody as active ingredient the particular compound embodied therein, and especially a pharmacologically acceptable salt thereof, for example, its tartrate, hydrochloride, hydrobromide, fumarate, or like pharmacologically acceptable salt.

As already stated, for oral use the compounds are usually administered as tablets, although other forms may be employed. Tablets may be made by compounding one of the compounds of the invention, preferably as an acid-addition salt, with customary carriers and adjuvents, e.g., talc, magnesium stearate, starch, lactose, gelatin, gums, or the like.

The following is a suitable tablet formulation:
0.1 - 1g of 4-(p-Fluorobenzoyl)-4-hydroxy-1-[4,4-(di-p-fluorophenyl)-butyl[-piperidine oxalate
9 g of potato starch
1 g of colloidal silica
2 g of talc
0.2 g of magnesium stearate
2.5 g of 5% aqueous solution of gelatin.

This mixture is made up into 100 tablets, each containing 1-10 mg of the active component.

The hydrochloride or other acid addition salts are readily soluble in water-isopropanol, which makes them particularly useful, since it enables the new compounds to be administered parenterally by injection.

For injection, the following solution is suitable:
5 - 500 mg of 4-(p-Methylbenzoyl)-4-hydroxy-1-[4,4-(di-p-fluorophenyl)butyl]-piperidine hydrochloride
dissolved in fifty milliliters of water and fifty milliliters of isopropanol containing 0.6 grams of sodium chloride.

The resulting solution is filled into ampules, each containing two milliliters of solution and thus 0.1 –10 milligrams of the active compound. The ampules are sterilized in the usual manner.

The pharmacologically active compounds provided by the present invention may also be administered successfully by embodying an effective quantity thereof in an injectable emulsion or suspension for injection into an animal body, in oral powders, suspension or syrups, and in other acceptable dosage forms.

Although very small quantities of the active materials of the present invention are effective when minor therapy is involved or in cases of administration to subjects having a relative low body weight, unit dosages are usually five milligrams or above and preferably twenty-five, fifty or one-hundred milligrams or even higher, depending of course upon the emergency of the situation and the particular result desired,. To repeat, the exact individual dosages as well as daily dosages in a particular case will of course be determined according to established medical principles and under the supervision of the physician or verterinarian involved.

Representative compounds of the invention, including important intermediates for their production, are set forth in Tables II, III and IV.

Various modifications in the compounds, compositions, and methods of the invention will be apparent to one skilled in the art and may be made without departing from the spirit or scope thereof, and it is therefore to be understood that the invention is to be limited only by the scope of the appended claims.

TABLE II

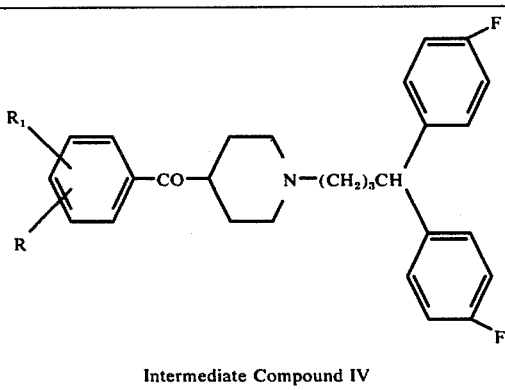

Intermediate Compound IV

| R | $R_1$ | Salt | Mp, °C[a] |
|---|---|---|---|
| H | 4-$CH_3$ | $(COOH)_2$ | 217–218 |
| H | 4-$OCH_3$ | $(COOH)_2$ | 199–200 |
| H | 4-F | $(COOH)_2$ | 228–229 |
| H | 4-Br | HBr | 145–147 |
| H | 3-$CF_3$ | HBr | 191–192 |
| 4-Cl | 3-$CF_3$ | HCl | 195–196 |

[a] Melting points are uncorrected

TABLE III

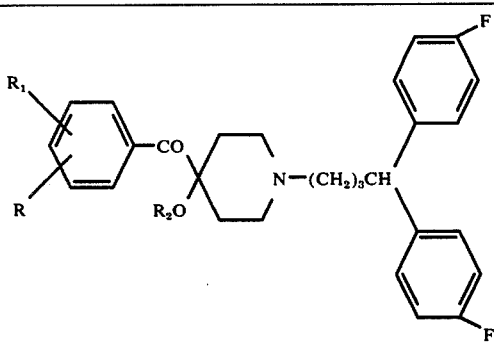

End Product I

| R | $R_1$ | $R_2$ | Salt | Mp, °C[a] |
|---|---|---|---|---|
| H | 4-$CH_3$ | H | HCl | 120–122 |
| H | 4-$OCH_3$ | H | $(COOH)_2$ | 192–195 |
| H | 4-F | H | $(COOH)_2$ | 214–216 |
| H | 4-Br | H | HCl | 165–167 |
| H | 3-$CF_3$ | H | $(COOH)_2$ | 152–155 |
| 4-Cl | 3-$CF_3$ | H | HCl | 238–240 |
| H | 4-F | $COC_2H_5$ | HCl | 246–248 |

[a] Melting points are uncorrected

TABLE IV

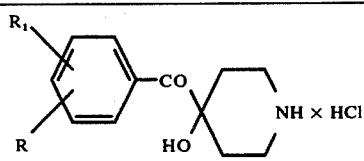

Intermediate Compound VII

| R | $R_1$ | Mp, °C[a] |
|---|---|---|
| H | 4-$CH_3$ | 232–235 |
| H | 4-$OCH_3$ | 218–220 |
| H | 4-F | 241–243 |

TABLE IV-continued

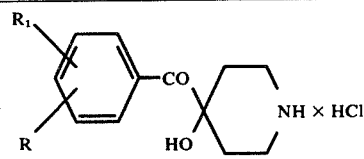

Intermediate Compound VII

| R | $R_1$ | Mp, °C[a] |
|---|---|---|
| H | 4-Br | 246–248 |
| 4-Cl | 3-$CF_3$ | 250 decomp. |
| H | H | 230–233 |
| H | 4-Cl | 205–208 |
| H | 3-$CF_3$ | 236 |

[a] Melting points are uncorrected

We claim:
1. A compound selected from the group consisting of (a) 4-benzoyl-4-hydroxy or acyloxy-1-(4,4-diphenylbutyl)-piperidines having the formula

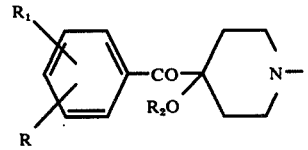

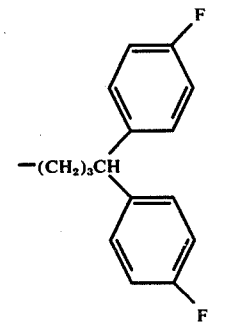

I wherein R and $R_1$ independently represent hydrogen, a lower-alkyl group of one to five carbon atoms inclusive, fluorine, chlorine, bromine, lower-alkoxy of one to five carbon atoms inclusive, or trifluoromethyl, and $R_2$ represents hydrogen or an acyl group of one to nineteen carbon atoms inclusive, and (b) acid addition salts thereof.

2. Pharmacologically acceptable addition salt of a basic piperidine ketone of claim 1.

3. Compound of claim 1 wherein $R_1$ is methyl and R is hydrogen.

4. Compound of claim 1 wherein $R_1$ is methoxy and R is hydrogen.

5. Compound of claim 1 wherein $R_1$ is fluoro and R is hydrogen.

6. Compound of claim 1 wherein $R_1$ is bromo and R is hydrogen.

7. Compound of claim 1 wherein $R_1$ is trifluoromethyl and R is hydrogen.

8. Compound of claim 1 wherein $R_1$ is hydrogen and R is hydrogen.

9. Compound of claim 1 wherein $R_1$ is chloro and R is hydrogen.

10. Compound of claim 1 wherein $R_1$ is chloro and R is trifluoromethyl.

11. Compound of claim 1 wherein $R_2$ is hydrogen.

12. Compound of claim 1 wherein $R_2$ is acyl.
13. Compound of claim 1 which is 4-(p-fluorobenzoyl)-4-hydroxyl-1-[4,4-(di-p-fluorophenyl)-butyl]-piperidine oxalate.
14. Compound of claim 1 which is 4-(p-fluorobenzoyl)-4-propionyloxy-1-[4,4-(di-p-fluorophenyl)-butyl]-piperidine hydrochloride.
15. Compound of claim 1 which is 4-(p-methylbenzoyl)-4-hydroxy-1-[4,4-(di-p-fluorophenyl)-butyl]-piperidine hydrochloride.
16. Compound of claim 1 which is 4-p-methoxybenzoyl)-4-hydroxy-1-[4,4-(di-p-fluorophenyl)-butyl]-piperidine oxalate.
17. Compound of claim 1 which is 4-(p-bromobenzoyl)-4-hydroxy-1-[4,4-(di-p-fluorophenyl)-butyl]-piperidine hydrochloride.
18. Compound of claim 1 which is 4-(m-trifluoromethyl)-benzoyl)-4-hydroxy-1-[4,4-(di-p-fluorophenyl)-butyl]-piperidine oxalate.
19. Compound of claim 1 which is 4-(3-trifluoromethyl-4-chlorobenzoyl)-4-hydroxy-1-[4,4-(di-p-fluorophenyl)-butyl]piperidine hydrochloride.
20. Compound of claim 1 which is 4-benzoyl-4-hydroxy-1-[4,4-(di-p-fluorophenyl)-butyl]-piperidine hydrochloride.
21. Compound of claim 1 which is 4-(p-chlorobenzoyl)-4-hydroxy-1-[4,4-(di-p-fluorophenyl)-butyl]-piperidine hydrochloride.
22. Compound of claim 1 which is 4-(p-fluorobenzoyl)-4-decanoyloxy-1-[4,4-(di-p-fluorophenyl)-butyl]-piperidine hydrochloride.
23. Compound of claim 1 which is 4-(p-fluorobenzoyl)-4-nondecanoyloxy-1-[4,4-(di-p-fluorophenyl)-butyl]-piperidine hydrochloride.
24. Compound of claim 1 which is 4-(p-fluorobenzoyl)-4-hydroxy-1-[4,4-(di-p-fluorophenyl)-butyl]-piperidine hydrochloride.
25. A pharmaceutical composition suitable for use in the alleviation of psychotic conditions comprising a compound of claim 1, in an amount effective for said purpose, in association with a pharmaceutical carrier.
26. Method for the treatment of a patient suffering from a psychotic condition, such as schizophrenic, manic, anxious, agony, or aggressive states, comprising administering to the patient a compound of claim 1 in an amount effective for the alleviation of said condition.
27. A compound selected from the group consisting of (a) 4-benzoyl-1-(4,4-diphenylbutyl)-piperidines having the formula

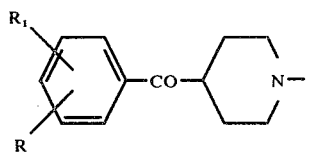

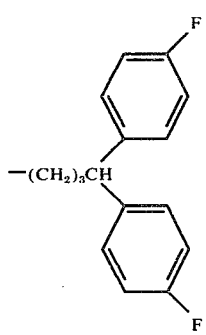

IV wherein R and $R_1$ independently represent hydrogen, a lower-alkyl group of one to five carbon atoms inclusive, fluorine, chlorine, bromine, lower-alkoxy of one to five carbon atoms inclusive, or trifluoromethyl, and (b) acid addition salts thereof.
28. Acid addition salt of a basic piperidine ketone of claim 27.
29. Compound of claim 27 wherein $R_1$ is methyl and R is hydrogen.
30. Compound of claim 27 wherein $R_1$ is methoxy and R is hydrogen.
31. Compound of claim 27 wherein $R_1$ is fluoro and R is hydrogen.
32. Comppund of claim 27 wherein $R_1$ is bromo and R is hydrogen.
33. Compound of claim 27 wherein $R_1$ is trifluoromethyl and R is hydrogen.
34. Compound of claim 27 wherein $R_1$ is trifluoromethyl and R is chloro.
35. Compound of claim 27 wherein $R_1$ is hydrogen and R is hydrogen.
36. Compound of claim 27 wherein $R_1$ is chloro and R is hydrogen.
37. Compound of claim 27 which is 4-(p-fluorobenzoyl)-1-[4,4-(di-p-fluorophenyl)-butyl]-piperidine acid addition salt.
38. Compound of claim 27 which is 4-(p-methylbenzoyl)-1-[4,4-(di-p-fluorophenyl)-butyl]-piperidine acid addition salt.
39. Compound of claim 27 which is 4-(p-methoxybenzoyl)-1-[4,4-(di-p-fluorophenyl)-butyl]-piperidine acid addition salt.
40. Compound of claim 27 which is 4-(m-trifluoromethylbenzoyl)-1-[4,4-(di-p-fluorophenyl)-butyl]-piperidine acid addition salt.
41. A compound selected from the group consisting of (a) 4-benzoyl-4-hydroxypiperidines having the formula

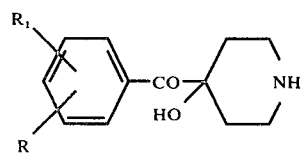

VII wherein R and $R_1$ independently represent hydrogen, a lower-alkyl group of one to five carbon atoms inclusive, fluorine, chlorine, bromine, lower-alkoxy of one to five carbon atoms inclusive, or trifluoromethyl, and (b) acid addition salts thereof.
42. Acid addition salt of a piperidine ketone of claim 41.
43. Compound of claim 41 wherein $R_1$ is methyl and R is hydrogen.
44. Compound of claim 41 wherein $R_1$ is methoxy and R is hydrogen.
45. Compound of claim 41 wherein $R_1$ is fluoro and R is hydrogen.
46. Compound of claim 41 wherein $R_1$ is bromo and R is hydrogen.
47. Compound of claim 41 wherein $R_1$ is trifluoromethyl and R is hydrogen.
48. Compound of claim 41 wherein $R_1$ is trifluoromethyl and R is chloro.

49. Compound of claim 41 wherein $R_1$ is hydrogen and R is hydrogen.

50. Compound of claim 41 wherein $R_1$ is chloro and R is hydrogen.

51. Compound of claim 41 which is 4-(p-fluorobenzoyl)-4-hydroxypiperidine acid addition salt.

52. Compound of claim 41 which is 4-(p-methylbenzoyl)-4-hydroxypiperidine acid addition salt.

53. Compound of claim 41 which is 4-(p-methoxybenzoyl)-4-hydroxypiperidine acid addition salt.

54. Compound of claim 41 which is 4-(m-trifluoromethylbenzoyl)-4-hydroxypiperidine acid addition salt.

* * * * *

UNITED STATES PATENT OFFICE
CERTIFICATE OF CORRECTION

Patent No. 4,024,264　　　　　Dated May 17, 1977

Inventor(s) Anders Karl Konrad Bjork et al

It is certified that error appears in the above-identified patent and that said Letters Patent are hereby corrected as shown below:

Col. 4, line 17: "4-benzoylipiperidine" should read ---4-benzoylpiperidine---
Col. 5, line 42: "4hydroxypiperidine VII," should read ---4-hydroxypiperidine VII,---
Col. 6, line 10: "the" should read ---The---
Col. 7-8, line 68-1: "13,(1)," should read ---13(1),---
Col. 8, line 67: was omitted should read ---4-(p-chlorobenzoyl)piperidine hydrochloride-- (App. pg. 14, line 4)
Col.10, line 63: "(di-p-fluorophenyl" should read ---(di-p-fluorophenyl)---
Col. 11, line 5: "-fluorphenyl)-" should read --- -fluorophenyl)----
Col. 11, line 65: "Nost" should read ---Most---
Col. 12, line 11: "-hydroxupiperidine" should read --- -hydroxypiperidine ---
Col. 12, line 16-17: "hydroxypiperidine" should read ---hydroxypiperidine hydrocholoride---
Col. 12, line 37: "as" should read ---was---

UNITED STATES PATENT OFFICE
CERTIFICATE OF CORRECTION

Patent No. 4,024,264                    Dated May 17, 1977

Inventor(s) Anders Karl Konrad Bjork et al

It is certified that error appears in the above-identified patent and that said Letters Patent are hereby corrected as shown below:

Col. 12, line 55: "-4hydroxy-" should read --- -4-hydroxy- ---
Col. 13, line 22: "methyl" should read ---methyl,---
Col. 13, line 23: "methoxy" should read ---methoxy,---
Col. 13, line 51: "havin" should read ---having---
Col. 14, line 50: "actue" should read ---acute---
Col. 15, line 4: "als" should read ---also---
Col. 15, line 34: "pill tablet," should read ---pill,tablet,---
Col. 16, line 25: "-butyl[-" should read --- - butyl]- ---
Col. 16, line 33: "hydrochloride" should read ---hydrochlorides ---
Col. 16, line 65: "verterinarian" should read ---veterinarian---
Col. 19, line 3: "hydroxyl-1-" should read ---hydroxy-1- ---
Col. 19, line 32: "-nondecanoyloxy-" should read ----nonadecanoyloxy- ---
Col. 20, line 14: "Comppund" should read ---Compound---

Signed and Sealed this

Sixth Day of June 1978

[SEAL]

Attest:

RUTH C. MASON
Attesting Officer

DONALD W. BANNER
Commissioner of Patents and Trademarks